United States Patent [19]

Katner

[11] Patent Number: 4,698,338
[45] Date of Patent: Oct. 6, 1987

[54] 7[2-(2-AMINOTHIAZOL-4-YL)-2-BENZYLOX-IMINO]ACETAMIDO-3[4-ALKYL-5-OXO-6-HYDROXY-3,4-DIHYDRO-1,2,4-TRIAZIN-3-YL]THIOMETHYL CEPHALOSPORINS

[75] Inventor: Allen S. Katner, Indianapolis, Ind.

[73] Assignee: Eli Lilly and Company, Indianapolis, Ind.

[21] Appl. No.: 831,033

[22] Filed: Feb. 19, 1986

[51] Int. Cl.$^4$ .................... A61K 31/545; C07D 501/36
[52] U.S. Cl. ........................................ 514/206; 540/227
[58] Field of Search .......................... 540/227; 514/206

[56] References Cited

U.S. PATENT DOCUMENTS

| | | | |
|---|---|---|---|
| 4,098,888 | 7/1978 | Ochiai et al. | 540/221 |
| 4,200,745 | 4/1980 | Katner | 540/221 |
| 4,279,793 | 7/1981 | Durckheimer et al. | 540/227 |
| 4,288,436 | 9/1981 | Takaya et al. | 540/227 |
| 4,304,770 | 12/1981 | Takaya et al. | 540/227 |
| 4,327,210 | 4/1982 | Montavon et al. | 540/227 |
| 4,425,340 | 1/1984 | Teraji et al. | 540/222 |
| 4,477,448 | 10/1984 | Hamberger et al. | 514/202 |

FOREIGN PATENT DOCUMENTS 852427  9/1977  Belgium .

Primary Examiner—Donald G. Daus
Assistant Examiner—Barbara Cassatt
Attorney, Agent, or Firm—William B. Scanlon; Leroy Whitaker

[57] ABSTRACT

O-Substituted oximinocephalosporins represented by the formula

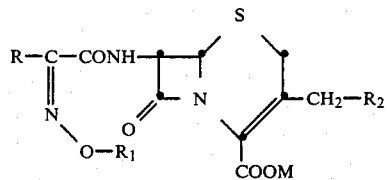

wherein R is a 5-membered or 6-membered heterocycle, preferably amino-substituted, e.g., 2-aminothiazol-4-yl, $R_1$ is an arylalkyl, aryloxyalkyl, or arylthioalkyl group, especially substituted benzyl; $R_2$ is a 1,2,4-triazin-3-yl thio group; and M is a salt or a biologically labile ester group; are potent antibacterial agents. Also provided are antibiotic formulations of said compounds and a method for treating infectious diseases in man or animals comprising the administration of said compounds.

13 Claims, No Drawings

7[2-(2-AMINOTHIAZOL-4-YL)-2-BENZYLOX-IMINO]ACETAMIDO-3[4-ALKYL-5-OXO-6-HYDROXY-3,4-DIHYDRO-1,2,4-TRIAZIN-3-YL]THIOMETHYL CEPHALOSPORINS

BACKGROUND OF THE INVENTION

This invention relates to semi-synthetic cephalosporin antibiotics. In particular, it relates to cephalosporin antibiotic compounds represented by the general formula 1

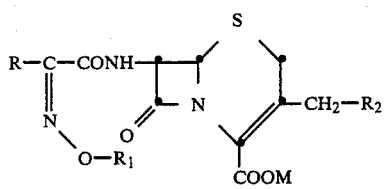

wherein R is a 5- or 6-membered heterocycle; $R_1$ is an aralkyl, aryloxyalkyl, or arylthioalkyl group; $R_2$ is a 1,2,4-triazine thio substituent; and M is hydrogen, a salt-forming cation, or a biologically labile ester group.

Cephalosporin antibiotics having an oximino group forming part of the 7-position side chain substituent are known. For example, U.S. Pat. No. 3,974,153 describes the methoximino cephalosporin known as cefuroxime; U.S. Pat. No. 4,098,888 describes oximino 3-heterocyclic thio cephalosporins; U.S. Pat. No. 4,152,432 describes the methoximino substituted cephalosporanic acid known as cefotaxime; U.S. Pat. No. 4,327,210 discloses the 3-thiazine thio substituted methoximino cephalosporin known as ceftriaxone; U.S. Pat. No. 4,427,674 describes 3-unsubstituted methoximino cephalosporins such as ceftizoxime. The oximino substituted cephalosporin antibiotics exhibit high antibacterial potency.

SUMMARY

O-Aralkyl, O-aryloxyalkyl, and O-arylthioalkyl heterocyclic oximino substituted 3-triazinethiomethyl cephalosporins represented by the formula 1 are broad spectrum semi-synthetic antibiotics exhibiting enhanced potency against streptococci and anaerobic bacteria. The compounds are prepared via nucleophilic displacement of a 3-halomethyl or 3-acyloxymethyl-3-cephem-4-carboxylic acid with a triazine represented by the formulae

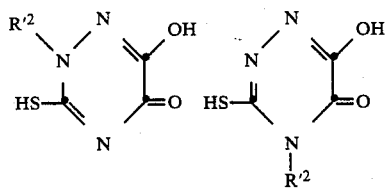

wherein $R'^2$ is $C_1$-$C_4$ alkyl. Preferred compounds are represented by the formula 1 wherein R is an amino-substituted 5-membered heterocycle and $R_1$ is an hydroxylated or chlorinated benzyl group.

Also provided is a method for treating bacterial infections in man and animals and pharmaceutical formulations comprising the antibiotics of the invention.

DETAILED DESCRIPTION

The antibiotics provided are represented by the above formula 1 wherein R is a 5-membered heterocycle represented by the formulae

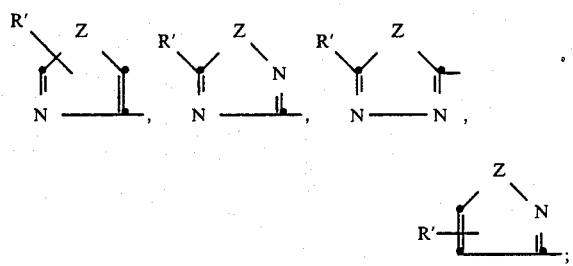

or a 6-membered heterocycle represented by the formulae

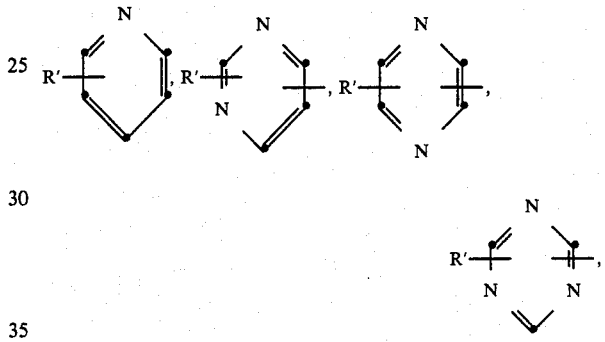

wherein
Z is O, S, or N—R" wherein R" is H, or methyl;
R' is hydrogen, amino, hydroxy, $C_1$-$C_4$ alkyl, or chloro;
$R_1$ is an arylalkyl, aryloxyalkyl, or arylthioalkyl group represented by the formula

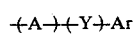

wherein A represents a straight or branched chain divalent $C_1$-$C_4$ alkylene radical; Y is O, S, or a carbon to carbon bond; and Ar represents a phenyl group

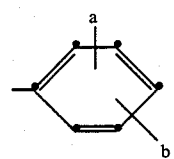

wherein a and b independently are hydrogen, halogen, hydroxy, amino, $C_1$-$C_4$ alkylamino, di($C_1$-$C_4$ alkyl) amino, $C_1$-$C_4$ alkylsulfonylamino, $C_1$-$C_4$ alkoxy, benzyloxy, carboxy, carboxymethyl, or trifluoromethyl; and a and b when bonded to adjacent ring carbon atoms can form a methylene dioxy radical

or Ar is a naphthyl group

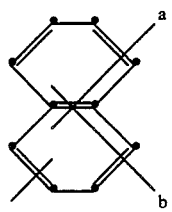

wherein a and b have the same meanings as defined above;

R₂ is a triazine thio group represented by the formulae

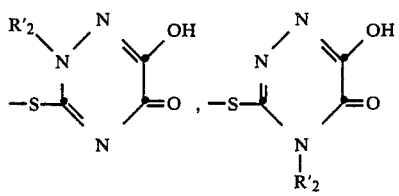

wherein $R_2'$ is $C_1$–$C_4$ alkyl; and M is hydrogen, a salt-forming cation, or a biologically labile ester group.

The heterocycle R (formula 1) is exemplified by thiazol-4-yl, 2-methylthiazole-4-yl, 2-chlorothiazol-4-yl, 2-aminothiazol-4-yl, 2-aminooxazol-4-yl, 2-ethyloxazol-4-yl, 2-hydroxythiazol-4-yl, 5-amino-1,2,4-thiadiazol-3yl, 5-chloro-1,2,4-oxadiazol-3-yl, 5-hydroxy-1,2,4-thiadiazol-3-yl, 2-aminopyrazole-4-yl, 5-methyl-1,2,4-triazol-3-yl, 1,2-dimethylpyrazol-4-yl, 5-chloro-1,3,4-thiadiazol-2-yl, 5-amino-1,3,4-thiadiazol-2-yl, 5-methyl-1,3,4-triazol-2-yl, 4-aminoimidazol-3-yl, 5-methylimidazol-3-yl, 1-methyl-4-aminoimidazol-3-yl, 4-aminoisothiazol-3-yl, 4-aminoisoxazol-3-yl, 2-aminopyridin-4-yl, 3-chloropyridin-3-yl, 2-aminopyrimidin-5-yl, 2-ethylpyrimidin-4-yl, 2-aminopyrazin-6-yl, 2-hydroxy-1,3,5-triazin-6-yl, and like substituted and unsubstituted heterocycles.

Preferred heterocycles are 5-membered heterocycles, e.g., the thiazole, oxazole, and 1,2,4-thia(oxa)diazoles. Preferably, the heterocycle is substituted by amino.

The substituent on the oximino oxygen atom $R_1$ is exemplified by the aralkyl groups, wherein Y is a carbon to carbon bond, such as benzyl, 4-hydroxybenzyl, 2,4-dihydroxybenzyl, 3,4-dihydroxybenzyl, 4-chlorobenzyl, 3-chloro-4-hydroxybenzyl, 3,4-dichlorobenzyl, 2,5-dichlorobenzyl, 4-bromobenzyl, 3-aminobenzyl, 4-trifluoromethylbenzyl, 4-carboxybenzyl, 3-ethoxybenzyl, 2-(4-hydroxyphenyl)ethyl, 1-(4-hydroxyphenyl)ethyl, 3-(3-hydroxyphenyl)propyl, 4-(3,4-dihydroxyphenyl)butyl, 2-(4-carboxyphenyl)ethyl, 2-(2,5-dichlorophenyl)ethyl, 2-(4-fluorophenyl)propyl, 3-(4-ethoxyphenyl)butyl, 1-naphthylmethyl, 2-naphthylmethyl, 4-hydroxynaphth-1-ylmethyl, 2-(4-hydroxynaphth-2-yl)ethyl, 3-(4,6-dichloronaphth-1-yl)propyl, 5-trifluoromethylnaphth-1-ylmethyl, 3-carboxy-7-chloronaphth-2-ylmethyl, and like aralkyl and Ar substituted aralkyl groups. When Y is O or S, the aryloxyalkyl and arylthioalkyl substituents are exemplified by groups such as phenoxymethyl, 4-hydroxyphenoxymethyl, 4-chlorophenoxymethyl, 4-isopropoxyphenoxymethyl, 3-trifluoromethylphenoxymethyl, 4-fluorophenoxymethyl, 3,5-dichlorophenoxymethyl, 2-phenoxyethyl, 2-(4-dimethylaminophenoxy)ethyl, 1-naphthyloxymethyl, 6-hydroxynaphth-1-yloxymethyl, 1-phenoxyethyl, 2,4-dihydroxyphenoxy, phenylthiomethyl, 3-hydroxyphenylthiomethyl, 3,4-dichlorophenylthiomethyl, 3,4-methylenedioxyphenylthiomethyl, 2-(4-fluorophenylthio)ethyl, 4-phenylthiobutyl, 2-(4-chlorophenylthio)propyl, 1-naphthylthiomethyl, 2-(naphth-2-ylthio)ethyl, and like groups.

Preferred oximino O-substituents are represented when $R_1$ is an aralkyl group or an Ar substituted aralkyl group, and Ar is phenyl or substituted phenyl. A further preferred group is represented when $R_1$ is benzyl, mono- or di-hydroxybenzyl, or a mono- or di-halobenzyl group.

The 1,2,4-triazine heterocycle in the 3'-position of a compound of the invention (formula 1) can exist in tautomeric forms, i.e., as the 5,6-diketo form or as the 5-keto-6-hydroxy form as shown below. Both tautomeric forms are encompassed within this invention though, for convenience, the 5-keto-6-hydroxy form is used in naming and in the structural formulae

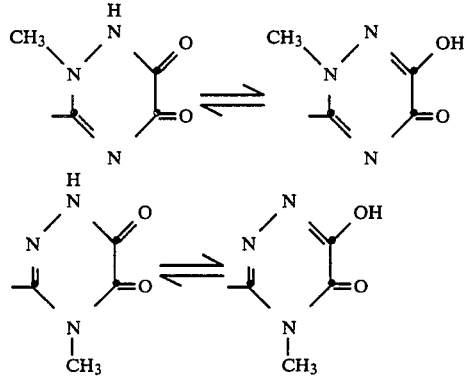

The salt-forming cation M of the formula 1 represents the alkali metal, alkaline earth metal, ammonium or substituted ammonium cations such as sodium, potassium, lithium, calcium, magnesium, ammonium, benzylammonium, dibenzylammonium, 2-hydroxyethylammonium, di-(2-hydroxyethyl)ammonium, a cation of a trialkyl or dialkylamine such as triethylammonium, di(n-butyl)ammonium, and like salt-forming cations. Preferred cations are the sodium and potassium cations. These salt forms of the compounds of the invention are useful forms of the antibiotic for preparing pharmaceutical formulations for administration of the antibiotics. The salt forms are also useful in the isolation and purification of the compounds in the free acid form.

The compounds of the invention as the free acids may be converted to a biologically labile ester derivative for use in administration, particularly by the oral route. Biolgically labile esters of the invention represented by M (formula 1) are the alkanoyloxyalkyl ester groups represented by the formula

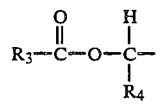

wherein $R_3$ is $C_1$–$C_4$ alkyl or phenyl, and $R_4$ is hydrogen or $C_1$–$C_3$ alkyl; the phthalidyl group; the indan-3-yl, or the 4,5-dimethyl-2-oxo-1,3-dioxolen-4'-yl cyclocarbonate group represented by the formula

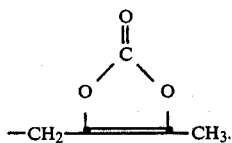

Examples of alkanoxyloxyalkyl ester groups are acetoxymethyl, 1-acetoxyethyl, 1-acetoxypropyl, propionoxymethyl, pivaloyloxymethyl, and the like.

The biologically labile esters are prepared with a compound of the formula 1 wherein M is hydrogen (free acid form) and an acyloxyalkyl halide in the presence of a base. For example, the free acid is reacted in DMF with pivaloyloxymethyl bromide in the presence of diethylaniline to form the pivaloyloxymethyl ester. Alternatively, an alkali metal salt of the cephalosporin acid, e.g., the sodium salt is reacted with the alkanoxyloxyalkyl halide to form the ester.

Preferred biologically labile esters are the pivaloyloxymethyl, acetoxymethyl, 1-acetoxyethyl, and 4,5-dimethyl-2-oxo-1,3-dioxolen-4'-yl groups.

The indan-3-yl ester is prepared in the same manner by alkylation with 3-bromoindane. The phthalidyl ester and the cyclocarbonate ester are prepared likewise by alkylation with the halide.

The cephalosporin antibiotics of this invention exist in the stereochemical form of the naturally produced compound cephalosporin C. The heterocycle in the 7-position side chain, in several instances, can exist in two tautomeric forms. For example, a 2-amino-substituted thiazole or oxazole can exist in the tautomeric forms shown below for the 2-aminothiazol heterocycle

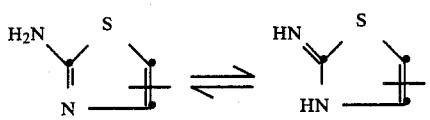

Such tautomeric forms are intended to be included herein.

The oximino group, $R_1O-N=C$, of the compounds can exist in two forms; the syn or Z form and the anti or E form. Owing to their enhanced antibacterial potency, the syn or Z form of the compounds is preferred. The compounds are readily obtained in the Z form when the N-acylation of 7ACA or the 3'-triazinethio-substituted 7-amino nucleus is carried out with the Z form of the oximino-substituted carboxylic acid or with a carboxy activating derivative thereof such as the HBT active ester.

The compounds of the formula 1 are illustrated in the following Table 1 wherein the terms in the headings refer to formula 1.

TABLE 1

| R | $R_1$ | $R_2{}^a$ |
|---|---|---|
| 2-aminothiazol-4-yl | benzyl | A |
| " | 4-hydroxybenzyl | A |
| " | 3,4-dihydroxybenzyl | A |
| " | 4-carboxybenzyl | A |
| " | 2-(4-hydroxyphenyl)ethyl | B |
| 2-aminooxazol-4-yl | 4-chlorobenzyl | A |
| " | 2,5-dichlorobenzyl | B |
| 2-hydroxy-1,3,4-thiadiazol-5-yl | benzyl | B |
| 2-amino-1,3,4-oxadiazol-5-yl | 4-fluorobenzyl | A |
| 2-aminopyrazol-4-yl | 2,4-dihydroxybenzyl | B |
| 2-methylpyrazol-4-yl | 3-(3-bromophenyl)propyl | A |
| 2-aminopyrimidin-5-yl | 4-carboxymethylbenzyl | B |
| 2-aminopyridin-4-yl | 3,4-dichlorobenzyl | A |
| " | 4-hydroxy-3-chlorobenzyl | B |
| 3-aminoimidazol-4-yl | benzyl | A |
| 2-chloro-1,3,4-triazol-5-yl | 3-dimethylaminobenzyl | A |
| 2-aminothiazol-4-yl | 4-chlorophenoxymethyl | B |
| " | 3,5-dihydroxyphenoxymethyl | A |
| 2-hydroxy-1,3,4-thiadiazol-5-yl | 2-(3-hydroxy-4-chlorophenyl)ethyl | A |
| 2-chlorothiazol-4-yl | phenylthiomethyl | B |
| 2-aminothiazol-4-yl | 4-methoxybenzyl | A |
| 2-aminooxazol-4-yl | 4-chlorophenylthiomethyl | B |
| 5-methyl-1,2,4-triazol-4-yl | 3-trifluoromethylphenylthiomethyl | B |
| 5-amino-1,2,4-triazol-3-yl | 2-(3-4-dihydroxyphenyl)propyl | B |

${}^a$A = 2-methyl-6-hydroxy-5-oxo-2,5-dihydro-1,2,4-triazin-3-ylthiol
B = 4-methyl-5-oxo-6-hydroxy-4,5-dihydro-1,2,4-triazin-3-ylthio Preferred compounds of the invention are represented by the formula 1 wherein R is 2-aminothiazol-4-yl or 2-aminooxazol-4-yl and $R_1$ is a phenylalkyl group or an Ar-substituted phenylalkyl group represented by the formula

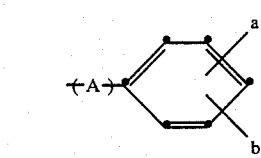

Preferably, A is $C_1-C_4$ alkylene and a and b are hydroxy or halo. Especially preferred compounds owing to their enhanced potency are represented by the formula 1 wherein R is 2-aminothiazol-4-yl, and $R_1$ is an hydroxylated benzyl group. Examples of these preferred compounds are represented by the formula

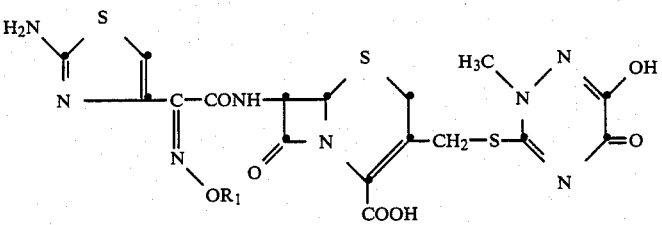

wherein $R_1$ is 4-hydroxybenzyl, 3-hydroxybenzyl, 2-hydroxybenzyl, 2,4-dihydroxybenzyl, 3,4-dihydroxybenzyl, or 3,5-dihydroxybenzyl, and the sodium and potassium salts thereof.

Also preferred are compounds wherein R is 2-aminothiazol-4-yl or 2-aminoxazole-4-yl, and $R_1$ is a halogenated benzyl group. Examples of halogenated benzyl groups of preferred compounds are 2-chlorobenzyl, 4-chlorobenzyl, 3-chlorobenzyl, 2,4-dichlorobenzyl, 3,4-dichlorobenzyl, 2,5-dichlorobenzyl, 3,5-dichlorobenzyl, 2-fluorobenzyl, 4-fluorobenzyl, 2,4-difluorobenzyl, 3-bromobenzyl, and 4-bromobenzyl. Two such preferred compounds are 7β-[2-(2-aminothiazol-4-yl)-2-(Z)-(4-chlorobenzyloxyimino)acetamido-]-3-[(2,5-dihydro-2-methyl-5-oxo-6-hydroxy-1,2,4-triazin-3-yl)thiomethyl]- 3-cephem-4-carboxylic acid, and 7β-[2-(2-aminothiazol-4-yl)-2-(Z)-(2,5-dichlorobenzyloxyimino)acetamido]-3-[(2,5-dihydro-2-methyl-6-hydroxy-5-oxo-1,2,4-triazin-3-yl)thiomethyl]-3-cephem-4-carboxylic acid.

Likewise, especially preferred compounds are represented by the above formula wherein the triazine thiol is of the formula

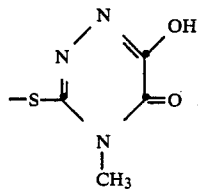

A further preferred group of antibiotics are represented by the formula

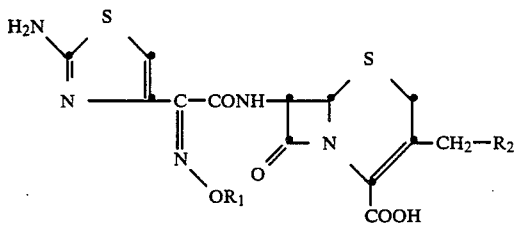

wherein $R_1$ is carboxybenzyl group represented by

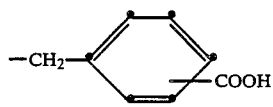

e.g., 4-carboxybenzyl or 3-carboxybenzyl; or $R_1$ is a carboxymethylbenzyl group represented by

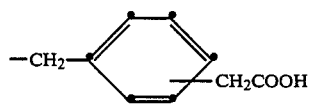

e.g., 4-carboxymethylbenzyl, 3-carboxymethylbenzyl, and 2-carboxymethylbenzyl; and $R_2$ has the same meanings as defined for formula 1.

The above preferred compounds of the invention are in the Z form (syn-isomer of oximino group).

The compounds of the invention inhibit the growth of microorganisms pathogenic to man and animals and can be used in the method described hereinafter for the treatment and prevention of infectious diseases.

The antibacterial activity of the compounds of the formula 1 is illustrated by the data presented in Table 2 for two such compounds. The data presented are the minimum inhibitory concentrations (μg/ml) against representative pathogens obtained in the standard agar dilution in vitro test.

TABLE 2

In Vitro Antibacterial Activity
Minimum Inhibitory Concentration (μg/ml)

| Microorganism | Test Compound A | Test Compound B |
|---|---|---|
| Staphylococcus aureus X1.1 | 1 | .5 |
| Staphylococcus aureus V41 | 8 | 4 |
| Staphylococcus aureus X400 | 16 | 32 |
| Staphylococcus aureus 513E | 8 | 4 |
| Staphylococcus epidermidis EPi1 | 8 | 8 |
| Staphylococcus epidermidis 222 | 2 | .5 |
| Streptococcus pyogenes C203 | <.008 | <.008 |
| Streptococcus pneumoniae Park I | <.008 | <.008 |
| Streptococcus Group D X66 | 128 | >128 |
| Streptococcus Group D 2041 | 1 | .5 |
| Haemophilus influenzae C.L. | .03 | .03 |
| Haemophilus influenzae 76 | — | .015 |
| Escherichia coli N10 | .25 | .25 |
| Escherichia coli EC14 | .125 | .25 |
| Escherichia coli TEM | .03 | .06 |
| Klebsiella pneumoniae X26 | .06 | .06 |
| Klebsiella pneumoniae KAE | 16 | 16 |
| Klebsiella pneumoniae X68 | .125 | .25 |
| Enterobacter aerogenes C32 | .25 | .25 |
| Enterobacter aerogenes EB17 | .5 | 1 |
| Enterobacter cloacae EB5 | .5 | .25 |
| Enterobacter cloacae 265A | 128 | 128 |
| Salmonella typhi X514 | .125 | .25 |
| Salmonella typhi 1335 | .25 | 1 |
| Pseudomonas aeruginosa X528 | 128 | 64 |
| Pseudomonas aeruginosa X239 | 8 | 8 |
| Pseudomonas aeruginosa PS18 | 16 | 32 |
| Pseudomonas aeruginosa PS72 | 64 | 16 |
| Serratia marcescens X99 | .5 | 1 |
| Serratia marcescens SE3 | 4 | 2 |
| Shigella sonnei N9 | .125 | .5 |
| Proteus morganii PR15 | 1 | .5 |
| Proteus inconstans PR33 | .125 | .25 |
| Proteus rettgeri C24 | .125 | .5 |
| Citrobacter freundii CF17 | 4 | 2 |
| Acinetobacter calcoaceticus AC12 | 16 | 2 |

A = 7β-[2-(2-aminothiazol-4-yl)-2-(4-hydroxybenzyloxyimino)acetamido]-3-[(2,5-dihydro-6-hydroxy-2-methyl-5-oxo-1,2,4-triazin-3-yl)thiomethyl]-3-cephem-4-carboxylic acid, Z form.
B = 7β-[2-(2-aminothiazol-4-yl)-2-(2,5-dichlorobenzyloxyimino)acetamido]-3-[(2,5-dihydro-6-hydroxy-2-methyl-5-oxo-1,2,4-triazin-3-yl)thiomethyl]-3-cephem-4-carboxylic acid, Z form.

The compounds of the invention are prepared by the N-acylation of 7-ACA followed by the displacement of the 3-acetoxymethyl group of the acylation product with the triazine thiol $R_2H$. The acylation is illustrated by the following reaction scheme.

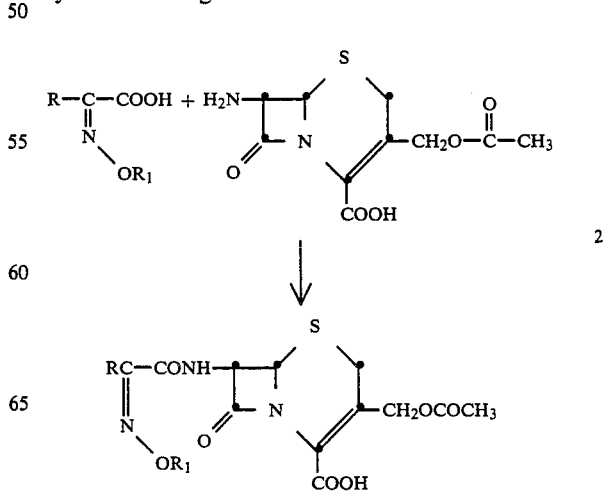

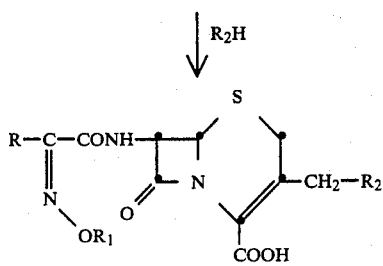

The acylation of 7-ACA is preferably carried out by forming the active ester of the acetic acid side chain moiety with hydroxybenztriazole. The active ester is prepared with the acid, HBT, and the condensing agent dicyclohexylcarbodiimide (DDC). The active ester is then used in the acylation of 7-ACA by known procedures.

Alternatively, the acetic acid side chain moiety can be converted to another active carboxy derivative for use in the acylation. For example, the acid may be converted to the acid chloride with oxalyl chloride or phosphorus oxychloride and the acid chloride used in the presence of a tertiary amine acid scavenger to acylate 7-ACA.

During the acylation, should the heterocycle R contain an amino substituent, the amino group is desirably protected with a conventional amino-protecting group. For example, the amino group of the heterocycle, 2-aminothiazole or 2-aminooxazole, can be protected with the triphenylmethyl (trityl) group or the t-BOC group during the acylation, and thereafter, it is conveniently removed with formic acid. Likewise, any hydroxy or carboxy groups present as substituents in $R_1$ are desirably protected to prevent any O-acylation or N-acylation in competition with the desired N-acylation of the 7-amino group of 7-ACA. Conventional hydroxy and carboxy-protecting groups may be used, e.g., for carboxy group protection the acid labile ester groups such as t-butyl can be used. Likewise, acid-sensitive hydroxy-protecting groups such as trityl, tetrahydropyranyl, 1-ethoxyethyl (formed with ethylvinyl ether), and the (2-methoxyethoxy)methoxy ether group can be used.

Preferably, these protecting groups are allowed to remain intact during the acylation and subsequent 3'-substitution reaction with the triazine thiol and are removed as the last step in the synthesis.

The acylation product 2 is then reacted with the desired triazine thiol, for example

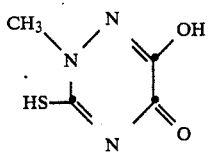

or an alkali metal salt thereof to provide the compound of formula 1. The reaction is the known nucleophilic displacement reaction of the 3'-acetoxy group by the thiol. The reaction can be carried out by the process of Hatfield, U.S. Pat. No. 4,144,391.

Alternatively, the 3'-acetoxy group of 2 can be converted to the 3-halomethyl derivative and the latter reacted with the triazine thiol. Preferably, the reaction is carried out by the process described by Bonjouklian, U.S. Pat. No. 4,266,049. According to this process, the acylation product 2 is silylated and the silyl derivative is converted to the 3-iodomethyl derivative with trimethylsilyl iodide (TMSI) as shown schematically below.

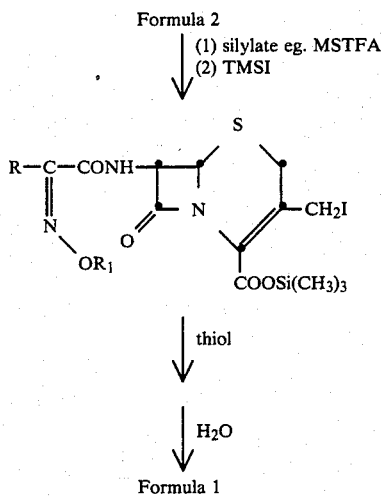

In an example of the preparation of a compound of the invention, α-benzyloxyimino-α-(2-tritylaminothiazol-4-yl)acetic acid is converted in an inert solvent to the HBT active ester with dicyclohexylcarbodiimide, and the active ester is allowed to react with 7-ACA to form 2 wherein R is 2-tritylaminothiazol-4-yl and $R_1$ is benzyl.

The acylation product is silylated with monotrimethylsilyltrifluoroacetamide (MSTFA) and the silylated derivative allowed to react with TMSI to form the 3-iodomethyl silylated derivative. The latter is reacted with the triazine thiol, e.g., 4-methyl-5-oxo-6-hydroxy-4,5-dihydro-1,2,4-triazin-3-thiol, to form the amino-protected compound of the formula 1. Treatment of the displacement product with 98% formic acid removes the trityl-protecting group to provide the compound represented by the formula 1 wherein R is 2-aminothiazol-4-yl, $R_1$ is benzyl, and $R_2$ is the 4-methyl-5-oxo-6-hydroxy-4,5-dihydro-1,2,4-triazin-3-ylthio group.

The compounds of the invention can be prepared by an alternative route which comprises carrying out the nucleophilic displacement of the 3'-acetoxy group of 7-ACA with triazine thiol and then N-acylating the 3-triazinethiomethyl 7-amino nucleus with the desired O-substituted oximino-acetic acid. The alternative route is preferably carried out as follows:

7-Aminocephalosporanic acid is N-formylated and the N-formyl-7-ACA is converted to the 3-iodomethyl derivative with TMSI. The 3-iodomethyl derivative is reacted with the triazine thiol to form the 7-formylamino-3-triazinethiomethyl-3-cephem-4-carboxylic acid, and the latter is hydrolyzed in methanolic HCl to remove the N-formyl group to provide the 7-amino-3-triazinethiomethyl nucleus compound. The alternative process is depicted in the following reaction scheme.

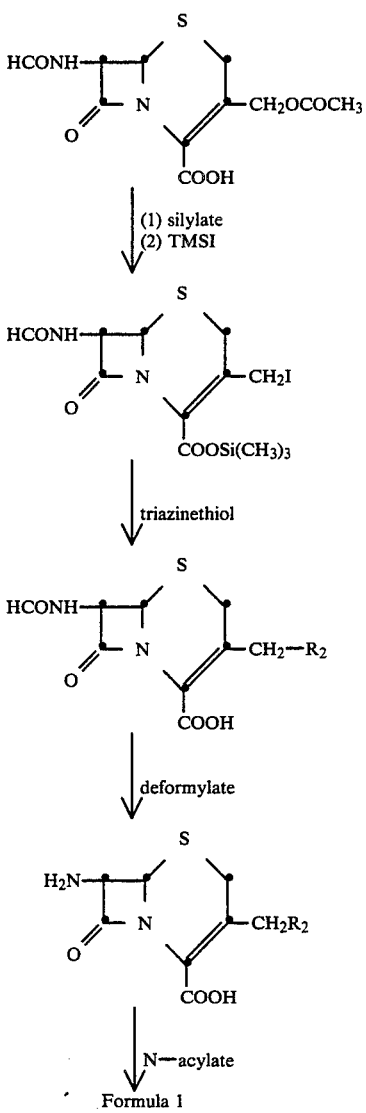

Formula 1

The triazine thiols used in the preparation of the compounds of the invention are prepared as described by Montavon et al., U.S. Pat. No. 4,327,210 and by Katner, U.S. Pat. No. 4,200,745.

As stated hereinabove, the compounds of the invention are useful in a method for the treatment and prevention of infectious diseases in man and animals. According to the method, a compound of the invention or a pharmaceutically-acceptable non-toxic salt or biologically labile ester thereof is administered in an antibiotically effective dose to a man or animal. An antibiotically effective dose is an amount of antibiotic compound of between about 25 mg and about 3.0 grams. The antibiotics may be administered in a single dose or in multiple doses throughout the day. For example, the antibiotic may be administered b.i.d., t.i.d., or q.i.d. and treatment may continue for days or for up to two weeks. The particular treatment regime used will depend on such factors as the nature and severity of the infection, the general health and age of the patient as well as the tolerance of the individual to the particular antibiotic.

The antibiotic may be administered orally, rectally, or parenterally, e.g., intramuscularly, intravenously, or subcutaneously. The compounds are preferably administered i.m. or i.v. for best results.

The method of this invention may be utilized after infection has occurred, or it may be used prophylactically prior to or shortly after exposure to an infectious organism. For example, the method may be utilized prior to abdominal surgery to ward off nosocomial infections.

The compounds of the invention are formulated into pharmaceutical formulations for use in the antibiotic method or for topical or other antibacterial use. The formulations provided herein comprise an antibiotically effective amount of a compound of the formula 1, a pharmaceutically acceptable non-toxic salt or biologically labile ester thereof and a pharmaceutical carrier.

Formulations for injectable (i.m.) use comprise a compound of the invention in a water soluble salt form, e.g., the sodium salt in a suitable diluent such as Water-For-Injection, Ringer's Solution, 5% dextrose, physiological saline, and the like. For i.v. use, the antibiotics may be made up in a larger volume of physiological fluid such as glucose solution and administered by the drip method or by piggyback administration.

For oral use, the antibiotic may be formulated into gelatin capsules e.g. in doses of 250 mg or 500 mg per capsule. Alternatively, the antibiotics may be formed into tablets of 200 mg, 300 mg, or 500 mg per tablet. Such tablets may contain fillers, lubricants, flavoring agents, solubilizing agents, and like excipients.

The antibiotics can be made up into liquid suspensions or solutions for pediatric and geriatric use. Such formulations may contain a concentration of antibiotic sufficient to achieve an antibiotically effective dose per 1 or 2 teaspoonsful of liquid. Suitable vehicles include water and aqueous ethanol and, in addition, may contain a suspending agent (for suspensions), a solubilizing agent (for solutions), a flavoring agent, a preservative, and like excipients.

The following Preparations and Examples further describe the invention.

In the Preparations and Examples, the following abbreviations are used: THF=tetrahydrofuran; DMSO=dimethylsulfoxide; MSTFA=mono-trimethylsilyltrifluoroacetamide; DMF=dimethylformamide; DME=1,2-dimethoxyethane; HBT=hydroxybenztriazole; DCC=dicyclohexylcarbodiimide; FAB=Fast Atom Bombardment.

The following Preparations 1–8 describe the preparation of the O-substituted oximino-acetic acid side chain moieties.

Preparation 1

α-(2,5-Dichlorobenzyloxyimino)-α-(2-tritylaminothiazol-4-yl)acetic acid

To a suspension of sodium hydride (50% in mineral oil, 1.5 g, 30 mmole) in 50 ml of DME and cooled in an ice bath was added dropwise with stirring a solution of 7.4 g (15 mmole) of ethyl α-hydroxyimino-2-(2-tritylaminothiazol-4-yl)acetate hydrochloride in 50 ml of DMF. The mixture was stirred for 45 minutes without cooling after the hydroxime was added. A solution of 3.5 g (15 mmole) of 2,5-dichlorobenzyl bromide in 35 ml of DME was added dropwise at room temperature and the reaction mixture was stirred overnight.

The reaction mixture was poured into a mixture of ice, 1N hydrochloric acid, and ethyl acetate and the organic layer was separated, washed sequentially with 1N HCl, water, and brine and dried over sodium sulfate. The dried organic layer was evaporated to yield a foam. The foam was dissolved in methylene chloride and the solution filtered through silica gel. The gel was eluted with methylene chloride and the filtrate and eluate were combined and evaporated to dryness. There were obtained 6.8 g of ethyl ester of the title compound as an orange glass. The filtration through silica gel was repeated to provide 5.3 g of product.

The ester product (5.3 g, 8.6 mmole) was suspended in 200 ml of ethanol containing 50 ml of 2N sodium hydroxide and the mixture was heated at the reflux temperature for one hour. The resultant solution was concentrated under vacuum to remove the ethanol, diluted with water, and acidified with concentrated hydrochloric acid. The acidified mixture was extracted twice with ethyl acetate and the combined extracts were washed once with water, once with brine, dried over sodium sulfate, and evaporated to dryness. There were obtained 5.49 g of the title acid.

Preparation 2

α-[4-(t-Butyloxycarbonyl)benzyloxyimino]-2-tritylaminothiazol-4-yl acetic acid

A suspension of sodium hydride in mineral oil (50%), 3.3 g (66.4 mmole) was cooled in an ice bath under nitrogen and 110 ml of DME were added followed by the dropwise addition of a solution of 16.4 g (33.1 mmole) of ethyl α-hydroxyimino-α-(2-tritylaminothiazol-4-yl)acetate hydrochloride in 110 ml of DMF. After the mixture was stirred in the cold for 45 minutes, a solution of 10.7 g (39.5 mmole) of 4-(t-butyloxycarbonyl)benzyl bromide in 50 ml of DME was added dropwise, and the mixture was stirred overnight at room temperature.

The reaction mixture was poured into 1 of water and extracted three times with ethyl acetate. The combined extracts were washed once with water, twice with 1N HCl, again with water, and with brine, dried and evaporated to yield 24.5 g of the O-alkylated ethyl ester as a red foam. The foam was dissolved in methylene chloride and filtered through silica gel eluting with methylene chloride. The filtrate and eluate wash were combined and evaporated to dryness. There were obtained 18.0 g of the ester as an orange semi-solid. The silica gel filtration was repeated to yield 13.6 g of the product ester.

The above ester product, 13.6 g (21 mmole) was saponified with 0.5N sodium hydroxide in ethanol to provide 9.6 g of the title acid.

Preparation 3

α-(4-Chlorobenzyloxyimino)-α-(2-tritylaminothiazol-4-yl)acetic acid

By following the procedures and by employing the conditions and reagents used in Preparations 1 and 2, 6.6 g (13.3 mmole) of ethyl α-hydroxyimino-α-(2-tritylaminothiazol-4-yl)acetate hydrochloride was alkylated with 3.2 g (15.6 mmole) of 4-chlorobenzyl bromide in the presence of sodium hydride. There were obtained about 9.0 g of the O-alkylated ester. Filtration through silica gel provided 7.5 g of the product.

The ester product was saponified to afford 6.65 g of the title acid.

Preparation 4

α-[4-[(2-Methoxyethoxy)methoxy]benzyloxyimino]-α-(2-tritylaminothiazol-4-yl)acetic acid A. 4-[(2-Methoxyethoxy)methoxy]benzyl bromide
Ethyl 4-hydroxybenzoate (21.3 g, 0.13 mmole) was O-alkylated in DME with 20 g (0.16 mmole) of 2-methoxyethoxymethyl chloride ($CH_3$—$CH_2CH_2O$—$CH_2Cl$) and sodium hydride. The reaction mixture was cooled in an ice bath and was diluted carefully with 20 ml of ethanol and with 50 ml of water. The mixture was concentrated by evaporation, diluted with water, and extracted twice with diethyl ether. The extracts were combined and washed once with water, once with brine, dried and evaporated to provice 34.1 g of ethyl 4-[(2-methoxyethoxy)methoxy]benzoate as an oil.

The above ethyl ester was saponified in 200 ml of ethanol and 200 ml of 2N sodium hydroxide by heating at the reflux temperature for two hours. The mixture was evaporated to remove the alcohol, diluted with water, and extracted with diethyl ether. The aqueous phase was acidifed with concentrated HCl and extracted twice with diethyl ether. The combined extracts were washed once with water, once with brine, dried and evaporated to yield 27.9 g of 4-[(2-methoxyethoxy)methoxybenzoic acid as a solid.

The benzoic acid product (15 g, 66 mmole) was dissolved in 75 ml of THF and the solution was cooled in an ice bath. To the cold solution was added dropwise 100 ml of 1M borane in THF (100 mmole) and the solution was stirred overnight at room temperature. The reaction mixture was cooled in an ice bath and treated dropwise with 130 ml of THF and 30 ml of water. The mixture was then evaporated to remove THF and the concentrate was extracted twice with diethyl ether. Thecombined extracts were washed once with 1N HCl, twice with water, and once with brine, were dried and evaporated to yield 7.0 g of the benzyl alcohol product as an oil. The aqueous phase turned cloudy and was extracted and washed up as before to yield an additional 1.3 g of the product, 4-[(2-methoxyethoxy)methoxy]benzyl alcohol.

The above benzyl alcohol product (8.3 g, 39 mmole) was dissolved in 50 ml of diethyl ether and 8.6 ml of pyridine (108 mmole) were added. The solution was cooled in an ice bath and a solution of 9.0 g (43 mmole) of thionyl bromide in 30 ml of diethyl ether was added dropwise. The solution was stirred for one hour in the cold, was diluted with water, and the organic phase separated. The aqueous phase was extracted with diethyl ether and the extract combined with the organic phase. The organic phase was washed with 1N HCl, water and brine, dried and evaporated to yield 6.6 g of 4-[(2-methoxyethoxy)methoxy]benzyl bromide as an oil.

B. Ethyl α-[4-[(2-methoxyethoxy)methoxy]benzyloxyimino]-α-(2-tritylaminothiazol-4-yl)acetate Ethyl α-hydroxyimino-α-(2-tritylaminothiazol-4-yl)acetate hydrochloride (11.8 g, 24 mmole) was O-alkylated in DME (sodium hydride) with 6.6 g (24 mmole) of the benzyl bromide product obtained as described in A above to provide 6.2 g of the O-alkylated ethyl ester B.

The ethyl ester B (6.2 g, 9.5 mmole) was saponified in 100 ml of methanol with 50 ml of 5N sodium hydroxide by heating at the reflux temperature for 1.5 hours. The reaction mixture was evaporated to remove methanol, diluted with water, acidified with 1N HCl, and extracted three times with methylene chloride. The combined extracts were washed with water and with brine, were dried and evaporated to yield 5.3 g of the title compound.

Preparation 5

α-Benzyloxyimino-α-(2-tritylaminothiazol-4-yl)acetic acid

The title compound was obtained by O-alkylating 5.9 g (12 mmole) of ethyl α-hydroxyimino-α-(2-tritylaminothiazol-4-yl)acetate with 2.05 g (12 mmole) of benzyl bromide, according to the procedures described in the above Preparations. The O-benzyl ethyl ester was saponified to provide 5.8 g of the title compound.

Preparation 6

α-(1-Naphthylmethoxyimino)-α-(2-tritylaminothiazol-4-yl)acetic acid

The title compound was prepared with 1-napthylmethyl bromide by following the O-alkylation and saponification procedures and employing the starting material and reagents as described in the above Preparations.

Preparation 7

α-[4-(Benzyloxy)benzyloxyimino]-α-(2-tritylaminothiazol-4-yl)acetic acid

The title compound was prepared with 4-benzyloxybenzyl bromide by following the O-alkylation and saponification procedures described in the foregoing Preparations.

Preparation 8

α-(4-Methoxybenzyloxyimino)-α-(2-tritylaminothiazol-4-yl)acetic acid

The title compound was prepared with 4-methoxybenzyl bromide by following the O-alkylation and saponification procedures described by the preceding Preparations. There were obtained 2.5 g of the title acid as cream-colored crystals melting at about 134° C. to about 137° C. from ethanol.

The following Preparations 9–14 describe the preparations of the 7β-[2-(heterocyclic)-2-oximinoacetamido]-3-acetoxymethyl-3-cephem-4-carboxylic acids used in the preparation of compounds of the invention.

Preparation 9

7β-[2-(2-Aminothiazol-4-yl)-2-(2,5-dichlorobenzyloxyimino)acetamido]-3-acetoxymethyl-3-cephem-4-carboxylic acid The 2,5-dichlorobenzyloxyiminoacetic acid (Preparation 1), 1.38 g, 2.4 mmole, and 361 mg (2.4 mmole) of HBT were suspended in 5 ml of methylene chloride and 486 mg (2.4 mmole) of DCC were added. The mixture was stirred for two hours at room temperature, filtered, the filtrate evaporated, and the residue dissolved in 10 ml of acetone and 5 ml of THF. 7-Aminocephalosporanic acid, 653 mg (2.4 mmole), was suspended in 15 ml of water, 7.5 ml of acetone added, and the pH adjusted to 7.5 with 45% aqueous potassium phosphate. The above solution of the imino-acetic acid HBT ester was added to the 7-ACA solution, and the acylation mixture was stirred overnight at room temperature.

The reaction mixture was filtered, evaporated to remove organic solvents and 1 ml of 45% $K_3PO_4$ solution was added to maintain solution. The mixture was diluted with water and extracted twice with ethyl acetate. The combined extracts were dried over sodium sulfate and evaporated to dryness. The residue was dissolved in methylene chloride and the solution was washed with 1N HCl, once with brine, was dried and evaporated to dryness. There were obtained 1.5 g of the title compound as the amino-protected trityl derivative.

The trityl-protected acylation product, 1.5 g (1.8 mmole), was dissolved in 10 ml of 98% formic acid and 2 drops of water were added to the solution. The solution was stirred for 1.5 hours at room temperature, filtered to remove trityl alcohol, and evaporated to dryness. Diethyl ether was added to the residue and the product crystallized and was filtered. There were obtained 790 mg of the title compound as a powder.

IR: 1775 cm$^{-1}$ (β-lactam carbonyl).

UV: λmax 226.

Mass Spectrum: (FAB) M+ 600.

Elemental Analysis: Theory: C, 44.01; H, 3.19; N, 11.66; Cl, 11.81. Found : C, 43.83; H, 3.13; N, 11.45; Cl, 11.45.

Preparation 10

7β-[2-(2-Aminothiazol-4-yl)-2-(4-carboxybenzyloxyimino)acetamido]-3-acetoxymethyl-3-cephem-4-carboxylic acid The imino acetic acid, Preparation 2, was used to acylate 7-ACA with HBT-DCC by the procedure of Preparation 9, and the acylation product was deprotected stepwise with 98% formic acid and then with trifluoroacetic acid-anisole to provide the title compound.

Preparation 11

7β-[2-(2-Aminothiazol-4-yl)-(4-chlorobenzyloxyimino)acetamido]-3-acetoxymethyl-3-cephem-4-carboxylic acid By following the acylation method of Preparation 9, the imino-acetic acid side chain of Preparation 3 was used to acylate 7-ACA to provide the title compound as the trityl-protected derivative. The trityl group was removed with 98% formic acid to yield the title compound.

Preparation 12

7β-[2-(2-Aminothiazol-4-yl)-2-(4-hydroxybenzyloxyimino)acetamido]-3-acetoxymethyl-3-cephem-4-carboxylic acid The title compound was prepared with the di-protected imino-acetic acid of Preparation 4B and 7-ACA by the acylation method of Preparation 9 to provide the deprotected acylation product. The trityl and 4-(2-methoxyethoxy)methoxy-protecting groups were both removed upon treatment of the deprotected acylation product with 98% formic acid for 3 hours at room temperature to provide the title compound.

Preparation 13

7β-[2-(2-Aminothiazol-4-yl)-2-benzyloxyimino-acetamido-3-acetoxymethyl-3-cephem-4-carboxylic acid The title compound was obtained with the benzyloxyiminoacetic acid of Preparation 5 and 7-ACA by the acylation and trityl-protecting group removal methods of Preparation 9.

Preparation 14

7β-[2-(2-Aminothiazol-4-yl)-2-(1-naphthylenethoxyimino)acetamido]-3-acetoxymethyl-3-cephem-4carboxylic acid The title compound was prepared with the 1-naphthylmethoxyiminoacetic acid of Preparation 6 and Preparation 9.

EXAMPLE 1

7β-[2-(2-Aminothiazol-4-yl)-2-(4-hydroxybenzyloxyimino)acetamido]-3-[(2,5-dihydro-6-hydroxy-2-methyl5-oxo-1,2,4-triazin-3-yl)thiomethyl]-3-cephem-4carboxylic acid To a suspension of 205 mg (0.4 mmole) of 7β-[2-(2-aminothiazol-4-yl)-2-(4-hydroxybenzyloxyimino)acetamido]-3-acetoxymethyl-3-cephem-4-carboxylic acid in 5 ml of methylene chloride and under nitrogen was added 0.5 ml of MSTFA and the mixture warmed to 40° C. for 5 minutes. After cooling to room temperature, the solution obtained was treated with 0.15 ml (1 mmole) of TMSI and the solution stirred for 30 minutes. The reaction mixture was evaporated to dryness and the silylated 3-iodomethyl product residue was dissolved in 5 ml of acetonitrile and the solution treated with 0.14 ml of THF to destroy excess TMSI.

A solution of 70 mg (0.44 mmole) of 2,5-dihydro-6-hydroxy-2-methyl-5-oxo-1,2,4-triazine-3-thiol in 1 ml of acetonitrile containing 0.25 ml of MSTFA was added to the solution of the 3-iodomethyl cephalosporin derivative and the mixture was stirred for 3 hours at room temperature. Two drops of water were then added, the mixture stirred for 30 minutes and filtered to yield 160 mg of the crude title compound.

The product was dissolved in an aqueous solution of sodium bicarbonate and chromatographed over a $C_{18}$ reverse phase column using 30% acetonitrile:$H_2O$:2% acetic acid for elution. All fractions containing the product were combined and lyophilized to yield 60 mg of the title compound.

MS: M+647.

EXAMPLE 2

7β-[2-(2-Aminothiazol-4-yl)-2-(4-chlorobenzyloxyimino)acetamido]-3-[(2,5-dihydro-6-hydroxy-2-methyl-5-oxo-1,2,4-triazin-3-yl)thiomethyl]-3-cephem-4-carboxylic acid To a suspension of 200 mg (0.35 mmole) of 7β-[2-(2-aminothiazol-4-yl)-2-(4-chlorobenzyloxyimino)acetamido]-3-acetoxymethyl-3-cephem-4-carboxylic acid in 5 ml of methylene chloride was added 0.5 ml of MSTFA and the suspension was stirred at 40° C. until solution occurred. The solution was cooled to room temperature and 0.13 ml (0.87 mmole) of TMSI was added. The reaction stirred at room temperature for 30 minutes and evaporated to an oil. The oil was dissolved in 3 ml of acetonitrile and 0.12 ml (1.5 mmole) of THF was added. The mixture was then stirred at room temperature for 5 minutes to destroy excess TMSI and provide in solution the corresponding 3-iodomethyl-3-cephem derivative.

To the solution of the 3-iodomethyl-3-cephem was added a solution of 65 mg (0.4 mmole) of 2,5-dihydro-6-hydroxy-2-methyl-5-oxo-1,2,4-triazine-3-thiol in 1 ml of acetonitrile, prepared with 0.25 ml of MSTFA, and the mixture was stirred at room temperature for 3 hours. The reaction mixture then was treated with three drops of water, the precipitate filtered and dried to yield 240 mg of crude title compound.

The product was dissolved in DMSO and chromatographed over a $C_{18}$ reverse phase column using 30% acetonitrile:water:2% acetic acid for elution. The fractions containing the product were combined, concentrated to a small volume by evaporation, and the concentrate lyophilized to yield 100 mg of the title compound.

IR: 1772 cm$^{-1}$(β-lactam carbonyl).
UV: λmax 225 ε29855.
MS (FAB): M+665.

EXAMPLE 3

7β-[2-(2-Aminothiazol-4-yl)-2-(2,5-dichlorobenzyloxyimino)acetamido]-3-[(2,5-dihydro-6-hydroxy-2-methyl-5-oxo-1,2,4-triazin-3-yl)thiomethyl]-3-cephem-4-carboxylic acid The title compound was prepared by following the reaction procedures and conditions used in Examples 1 and 2. There were obtained 100 mg of the lyophilized title compound after chromatography over a $C_{18}$ reverse phase column using 40% acetonitrile, water, 2% acetic acid for elution.

IR: 1774 cm$^{-1}$ (β-lactam carbonyl).
UV: λmax 229ε35398.
MS (FAB): M+699.

EXAMPLE 4

7β-[2-(2-Aminothiazol-4-yl)-2-(4-carboxybenzyloxyimino)acetamido]-3-(2,5-dihydro-6-hydroxy-2-methyl-5-oxo-1,2,4-triazin-3-yl)thiomethyl]-3-cephem-4-carboxylic acid By following the procedures and conditions of Example 2, 335 mg (0.58 mmole) of 7β-[2-(2-aminothiazol4-yl)-2-(4-carboxybenzyloxyimino)acetamido]-3-acetoxymethyl-3-cephem-4-carboxylic acid was silylated with MSTFA and converted to the 3-iodomethyl silylated derivative. The latter was reacted with 102 mg of the thiol to yield 130 mg of the title compound followin $C_{18}$ reverse phase chromatography.

EXAMPLE 5

7β2-(2-Aminothiazol-4-yl)-2-(1-naphthylmethoxyimino)acetamido]-3-[(2,5-dihydro-6-hydroxy-2-methyl-5-oxo-1,2,4-triazin-3-yl)thiomethyl]-3-cephem-4-carboxylic acid To a suspension of 210 mg (0.36 mmole) of 7β-[2-(2-aminothiazol-4-yl)-2-(1-naphthylmethoxyamino)acetamido]-3-acetoxymethyl-3-cephem-4-carboxylic acid in 5 ml of methylene chloride was added 0.25 ml of MSTFA. When the solution had formed, TMSI (0.15 ml, 1 mmole) was added and the solution was stirred for 30 minutes at room temperature. The solution was evaporated to provide the silylated 3-iodomethyl derivative as an oil. The oil was dissolved in 3 ml of acetonitrile, 0.14 ml of THF was added and the mixture was stirred for 5 minutes at room temperature.

A suspension of 70 mg (0.44 mmole) of 2,5- dihydro-6-hydroxy-2-methyl-5-oxo-1,2,4-triazin-3-thiol in 1 ml of acetonitrile was treated with 0.25 ml of MSTFA and sonicated to form a solution. The solution was added to the solution of the 3-iodomethyl derivative and the mixture was stirred for 3 hours at room temperature. Two drops of water were added to the mixture and the product precipitated. The product, 200 mg, was filtered, dissolved in DMSO and chromatographed over a $C_{18}$ silica gel reverse phase column using acetonitrile:water:acetic acid, 4:58:2, % by volume. There were obtained 85 mg of the chromatographed title compound.

IR: 1774 cm$^{-1}$ ($\beta$-lactam carbonyl).
5 UV: $\lambda$max 270 and 222.
MS (FAB): M$^+$681.

EXAMPLE 6

7$\beta$2-(2-Aminooxazol-4-yl)-2-(4-hydroxybenzyloxyimino)acetamido]-3-[(2-methyl-5-oxo-6-hydroxy-2,5-dihydro-1,2,4-triazin-3-yl)thiomethyl]-3-cephem-4-carboxylic acid The title compound is prepared by using the procedures and conditions described by Example 1 with 7$\beta$-[2-(2-aminooxazole-yl)-2-(4-hydroxybenzyloxyimino)acetamido]-3-acetoxymethyl-3-cephem-4-carboxylic acid and 2-methyl-5-oxo-6-hydroxy-2,5-dihydro-1,2,4-triazine-3-thiol.

I claim:

1. The compound of the formula

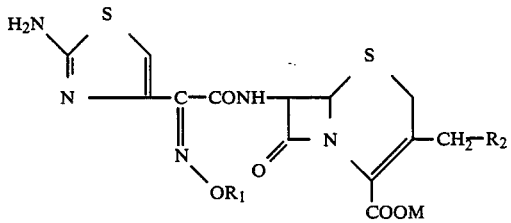

wherein
R$^1$ is a group of the formula

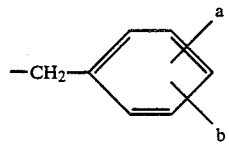

wherein a and b independently are hydrogen, hydroxy or halo provided that one of a or b is other than hydrogen, R$^2$ is a triazine thio group of the formulae

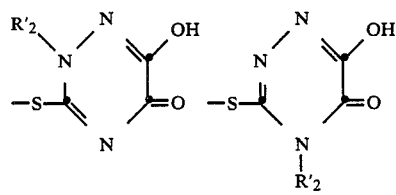

wherein R'$_2$ is C$_1$–C$_4$ alkyl; and
M is hydrogen, a salt-forming cation or the residue of a biologically labile ester group.

2. The compound of the formula

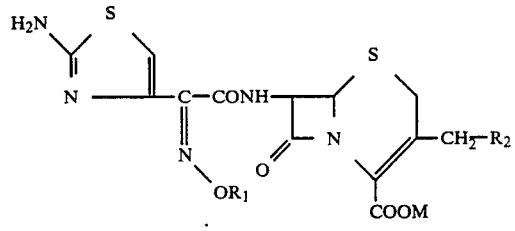

wherein
R$_1$ is a group of the formula

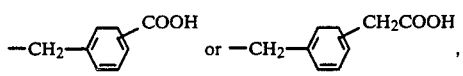

R$_2$ is a triazine thio group of the formulae

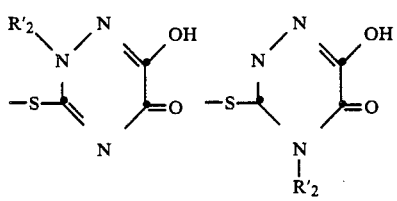

wherein R'$_2$ is C$_1$–C$_4$ alkyl; and
M is hydrogen, a salt-forming cation or the residsue of a biologically labile ester group.

3. The compound of claim 1 wherein one or both of a and b is or are chloro.

4. The compound of claim 3 which is 7$\beta$-[2-(2-aminothiazol-4-yl)-2-(Z)-(4-chlorobenzyloxyimino)-acetamido]-3-[(2,5-dihydro-6-hydroxy-2-methyl-5-oxo1,2,4-triazin-3-yl)thiomethyl]-3-cephem-4-carboxylic acid.

5. The compound of claim 3 which is 7$\beta$-2-(2-amino-thiazol-4-yl)-2-(Z)-(2,5-dichlorobenzyloxyimino)-acetamido]-3-[(2,5-dihydro-6-hydroxy-2-methyl-5-oxo-1,2,4-triazin-3-yl)thiomethyl]-3-cephem-4-carboxylic acid.

6. The compound of claim 1 wherein one or both of a and b is or are hydroxy.

7. The compound of claim 6 which is 7$\beta$-[2-(2-aminothiazol-4-yl)-2-(Z)-(4-hydroxybenzyloxyimino)-acetamido]-3-[(2,5-dihydro-6-hydroxy-2-methyl-5-oxo1,2,4-triazin-3-yl)thiomethyl]-3-cephem-4-carboxylic acid.

8. The compound of claim 6 which is 7$\beta$[2-(2-aminothiazol-4-yl)-2-(Z)-(4-hydroxybenzyloxyimino)-acetamido]-3-[(4,5-dihydro-6-hydroxy-4-methyl-5-oxo1,2,4-triazin-3-yl)thiomethyl]-3-cephem-4-carboxylic acid.

9. The compound of claim 2 wherein one of a and b is carboxy or carboxymethyl.

10. The compound of claim 9 which is 7$\mu$-[(2-(2-aminothiazol-4-yl)-2-(Z)-4-carboxybenzyloxyimino)-acetamido]-3-[(2,5-dihydro-6-hydroxy-5-oxo-2-methyl1,2,4-triazin-3-yl)thiomethyl]-3-cephem-4-carboxylic acid.

11. The method for preventing or treating bacterial infections in man and animals which comprises administering to said man or animal an antibiotically effective amount of a compound of claim 1.

12. An antibiotic formulation which comprises an antibiotically effective amount of a compound of claim 1 and a pharmaceutically acceptable carrier.

13. The method for preventing or treating bacterial infections in man and animals which comprises administering to said man or animal an antibiotically effective amount of a compound of claim 2.

* * * * *